United States Patent [19]
Dickens et al.

[11] Patent Number: 4,691,710
[45] Date of Patent: Sep. 8, 1987

[54] MEDICAL APPARATUS AND SYSTEM

[76] Inventors: Judith F. Dickens, 3427 Pestalozzi, St. Louis, Mo. 63118; John J. Loughlin, 8145 Whitburn, St. Louis County, Mo. 63105

[21] Appl. No.: 830,080

[22] Filed: Feb. 18, 1986

[51] Int. Cl.$^4$ .............................................. A61B 5/02
[52] U.S. Cl. .................................. 128/673; 128/672; 33/379
[58] Field of Search ............................. 128/672–673, 128/674, 675, 748; 33/369, 379, 389

[56] References Cited

U.S. PATENT DOCUMENTS 3,996,927 12/1976 Frank ................................. 128/673
4,546,774 10/1985 Haught ............................... 128/673

OTHER PUBLICATIONS

Corbett et al.; "A Self-Levelling Central Venous Electro-Manometer"; *Med. and Biol. Engr.*, vol. 12, No. 3, 5-1974, p. 366.

Primary Examiner—Kyle L. Howell
Assistant Examiner—Angela D. Sykes
Attorney, Agent, or Firm—Polster, Polster & Lucchesi

[57] ABSTRACT

A medical apparatus includes a light source for casting a light pattern upon a patient. The light source is fixed vertically with respect to a reference such as the position of a transducer. The light source is movable about a horizontal axis once its vertical position is fixed to adjust the angle of the light pattern with respect to horizontal. A level is fixed with respect to the light source to indicate when the light source is level so that the position of the light pattern cast upon a patient indicates the relative vertical position of the patient with respect to the reference.

9 Claims, 8 Drawing Figures

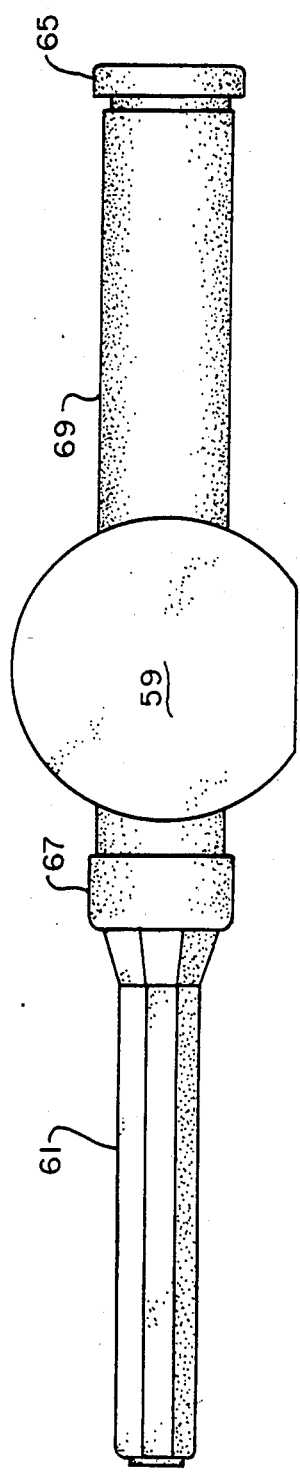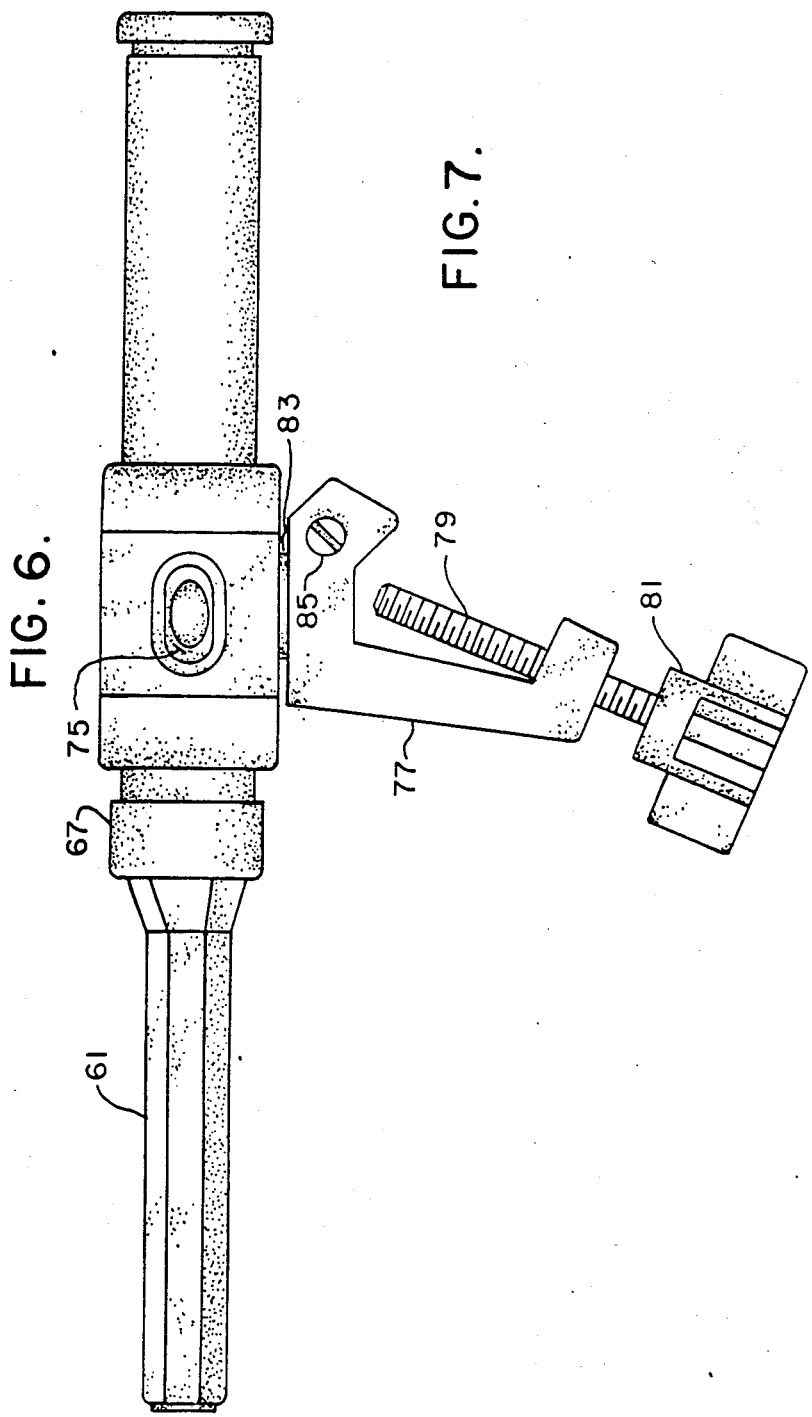

MEDICAL APPARATUS AND SYSTEM

BACKGROUND OF THE INVENTION

This invention relates in general to medical apparatus and more particularly, to medical apparatus especially for use in connection with taking internal pressure measurements of a patient.

In the management of critically ill patients, it has become common to monitor, on a continuous or regular basis, various pressures in the vessels of the patient. For example, monitoring pulmonary artery and pulmonary capillary wedge pressures with a catheter (such as the one sold by American Edwards Laboratories under the trade designation SWAN-GANZ) to detect left ventricular failure is a standard procedure in many hospitals for management of critically ill patients. The proximal end of these catheters is placed in the vessel of the patient at the point where the pressure is to be measured. Catheters used in this way have a lumen which extends from a predetermined point on the catheter such as the end thereof back to the distal end of the catheter where it is connected to a pressure transducer. These pressure transducers are available from a variety of sources and include a strain gauge which converts the pressure present on a diaphragm of the transducer into an electrical signal for standard monitoring equipment. These pressure transducers are commonly mounted at a fixed vertical position on a movable structure near the patient, such as an IV pole. It is necessary for the transducer to be fixed vertically because otherwise movement of the transducer up or down the pole would result in a differing output from the transducer caused by the varying head of the fluid in the catheter. As can be appreciated, in the care of critically ill patients, it is desirable that the pressure readings taken by such transducers be consistent, accurate, and reliable.

Even though the transducer is fixed vertically with respect to the IV pole, the patient is not fixed with respect to the transducer. For example, the hospital bed in which the patient reclines may be moved upwardly or downwardly by a medical care professional for any number of reasons. In addition, mere movement of the patient on the bed can result in varying and inconsistent readings at the pressure transducer. For this reason, the vertical position of the patient with respect to the transducer must be kept fixed or at least periodically readjusted. However, since the transducer is spaced some distance from the patient, fixing of the relative vertical positions is not a simple task. At present, a carpenter's level of considerable length (three feet or more) is physically placed between the transducer and a predetermined point on the body of the patient each time readjustment is desired. The patient or the transducer is then moved vertically to provide the desired predetermined vertical spacing between the two.

The IV pole on which the transducer is mounted can be very crowded when the transducer is being used in connection with a patient in critical care. Thus, it is sometimes inconvenient to accurately place the carpenter's level in the proper position adjacent the pressure transducer to get an accurate measurement of the relative vertical positions of the transducer and the patient. Moreover, if the spacing between the patient and the pressure transducer is longer than the carpenter's level used to level the patient with respect to the transducer, the leveling will be only approximate. Conversely, if the distance is much shorter than the level, it could be necessary to either move the IV pole further away from the patient, or to have the carpenter's level extend past the pressure transducer. In any case, the large size of the carpenter's level makes it inconvenient to use in the confines of a critical care room.

SUMMARY OF THE INVENTION

Among the various objects and features of the present invention may be noted the provision of medical apparatus which facilitates fixing the vertical position of a patient with respect to a sensor, such as a pressure sensor.

Another object is the provision of medical apparatus which increases the consistency and reliability of pressure and other sensor measurements.

An additional object is to reduce the inconvenience to the critical care provider and the patient occasioned by the present apparatus.

A further object is the provision of medical apparatus which is equally usable over a range of transducer-patient distances.

Another object of the present invention is the provision of medical apparatus for fixing the vertical position of the patient with respect to a sensor such as a pressure transducer which is both accurate and relatively small in size.

Other objects and features will be in part apparent and in part pointed out hereinafter.

Briefly, medical apparatus of the present invention includes light source means for casting a light pattern upon a patient. Means are provided for fixing the vertical position of the light source means with respect to a reference. The light source means is movable about a horizontal axis once its vertical position is fixed to adjust the angle an axis of the light source makes with the horizontal. Level means are provided for indicating when the light source means is level so that the position of the light pattern cast upon a patient indicates the relative vertical position of the patient with respect to the reference.

The medical apparatus of this invention in included in a system which measures the internal pressures of a patient. The system, in addition to the medical apparatus outlined above, includes a pressure transducer, means spaced from the patient for fixedly mounting the pressure transducer, and a catheter having a lumen forming a fluid path between the pressure transducer and a point in the patient at which the pressure is to be measured.

The method of the present invention includes the steps of fixing a light source vertically with respect to a sensor, leveling the light source, and shining a light pattern from the source upon the patient. The relative position of the patient with respect to the sensor is adjusted until the light pattern strikes a predetermined position on the patient.

BRIEF DESCRIPTION OF THE DRAWINGS

FIG. 6 is a side elevation of the medical apparatus of the present invention;

FIG. 7 is a top plan of the medical apparatus of the present invention; and

Similar reference characters indicate similar parts throughout the several views of the drawings.

DESCRIPTION OF THE PREFERRED EMBODIMENT

Figure 1:
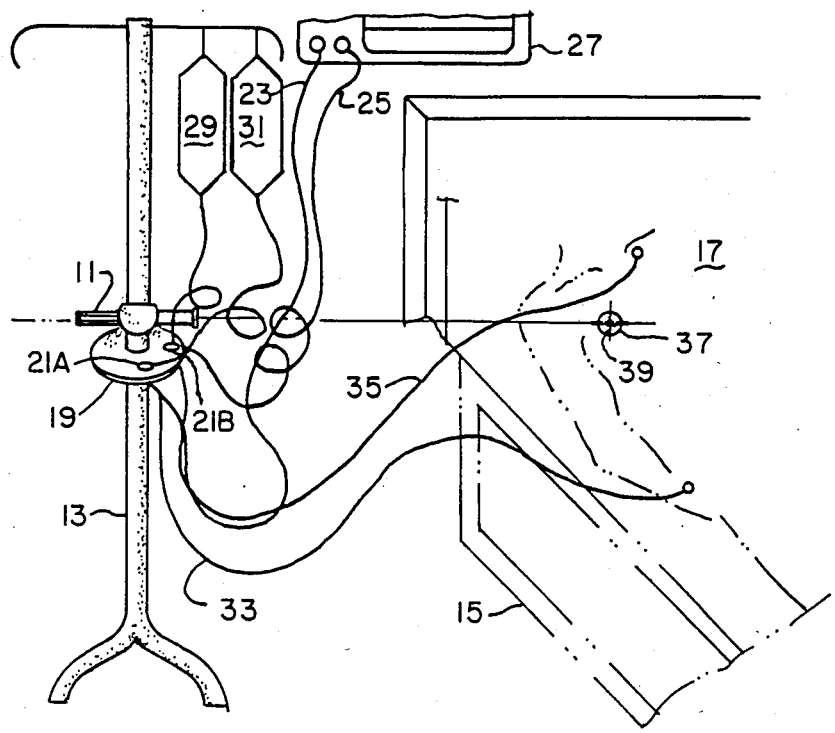
FIG. 1 is a perspective view illustrating the use of the medical apparatus and system of the present invention.

Turning now to the drawings, medical apparatus 11 of the present invention is shown secured to an upright support such as an IV pole 13 disposed a predetermined distance from a hospital bed 15 supporting a patient 17. Pole 13 also supports, immediately below medical apparatus 11, a platform 19. A pair of pressure transducers 21A and 21B are supported by platform 19. The transducers are electrically connected by wires 23 and 25 to a suitable monitor 27. A pair of bags 29 and 31 are supported in a conventional manner from pole 13. The bags contain a suitable solution, such as a heparin solution or the like. Pressure transducers 21A and 21B measure the pressure at two points in the body of patient 17. For example, transducer 21A is connected in the conventional manner to a catheter 33 which is inserted in the wrist of patient 17 to measure the arterial pressure of the patient. A catheter 35, such as a Swan-Ganz catheter, is in fluid communication with transducer 21B at one end, and is inserted below the clavicle of patient 17 to measure the pulmonary artery pressure of the patient.

Medical apparatus 11 includes a light source (see below) so that when the medical apparatus is activated, it casts a predetermined light pattern 37 on patient 17. The particular pattern cast by apparatus 11 is a dark spot in the middle of a bright circle, although any pattern could be used. Apparatus 11 is disposed a fixed distance on pole 13 above transducers 21A and 21B, so the position of light pattern 37 on patient 17 represents the distance vertically between the transducers and a desired position on the patient. For example, it is generally desirable to adjust the position of platform 19 so that the vent port (see below) of pressure transducers 21A and 21B are level with the patient's right atrium. Apparatus 11 facilitates this leveling by readily indicating the true vertical position of the patient with respect to the pressure transducers. The predetermined spot on patient 17 that light pattern 37 strikes when the patient and transducers are positioned properly is the same point that current critical care providers use in leveling the apparatus using a carpenter's level. For convenience and consistency in repositioning the patient as necessary, the critical care provider marks the patient with a mark 39 representing the desired target for the light pattern on the patient. Of course, other marks of suitable size and shape could also be used.

Figure 2:
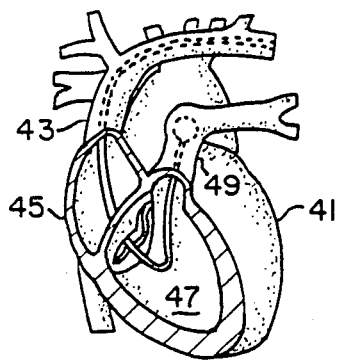
FIG. 2 is a schematic view illustrating one possible placement of a catheter using the system of the present invention.
Figure 3:
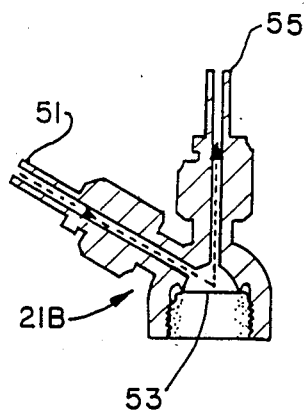
FIG. 3 is a schematic of the interior of a transducer which is usable with the medical apparatus of the present invention.

Turning to FIG. 2, catheter 35 is shown entering the heart 41 of patient 17 through the superior vena cava 43. The catheter passes through the right atrium 45 and right ventricle 47 to the pulmonary artery 49 where its lumen provides a fluid path from the pulmonary artery to transduce 21B. Changes in pressure in the pulmonary artery are supplied by catheter 35 to a port 51 (FIG. 3) of transducer 21B. A diaphragm 53 operatively connected in a conventional manner to a strain gauge (not shown) converts the pressure changes to an electrical signal supplied on cable or wire 25 to monitor 27. Also shown in FIG. 3 is a vent port 55 which in use is capped. It is vent port 55 which is leveled with the right atrium 45 of the patient. Of course, it should be understood that other points could be chosen on the transducer or the patient for the purpose of leveling the one with respect to the other. However, it is conventional to level the vent port of the transducer with the right atrium of the patient.

Figure 4:
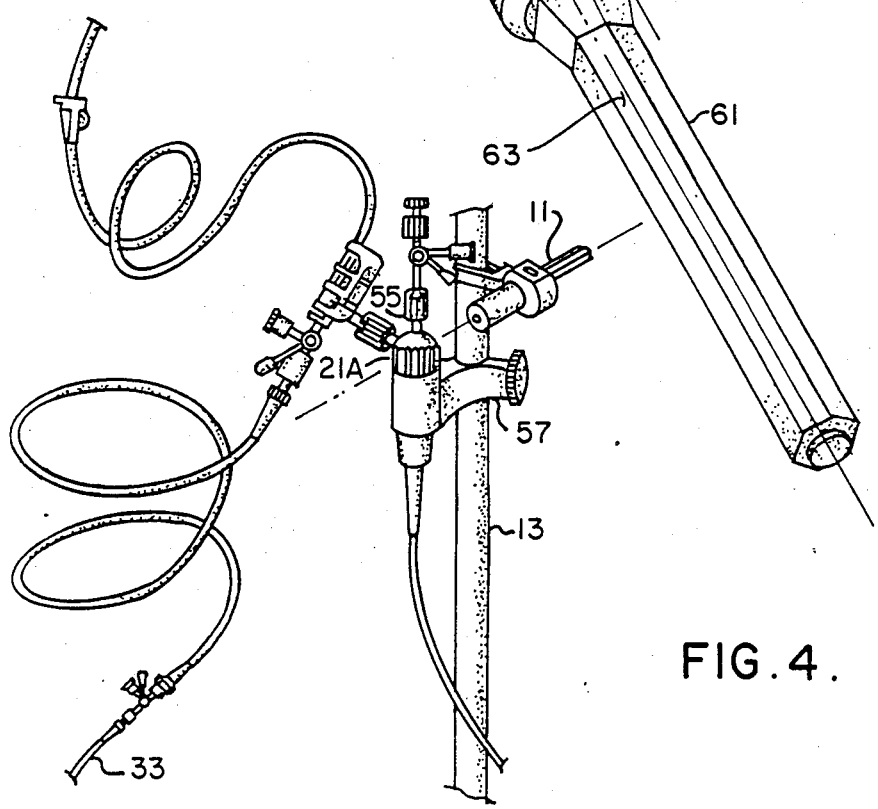
FIG. 4 is a perspective view similar to a portion of FIG. 1 illustrating the medical apparatus and system of the present invention.

An alternative mount 57 for transducer 21A is shown in FIG. 4. Such particular mounting arrangements for the transducers form no part of the present invention. FIG. 4 more clearly shows the medical apparatus 11 aligned with the vent port 55 of the transducer. If desired, apparatus 11 can be made integrally with mount 57 so that the vertical spacing of the apparatus and the transducer is accurately known, but it is preferred for flexibility that the apparatus 11 have its own mounting.

Figure 5:
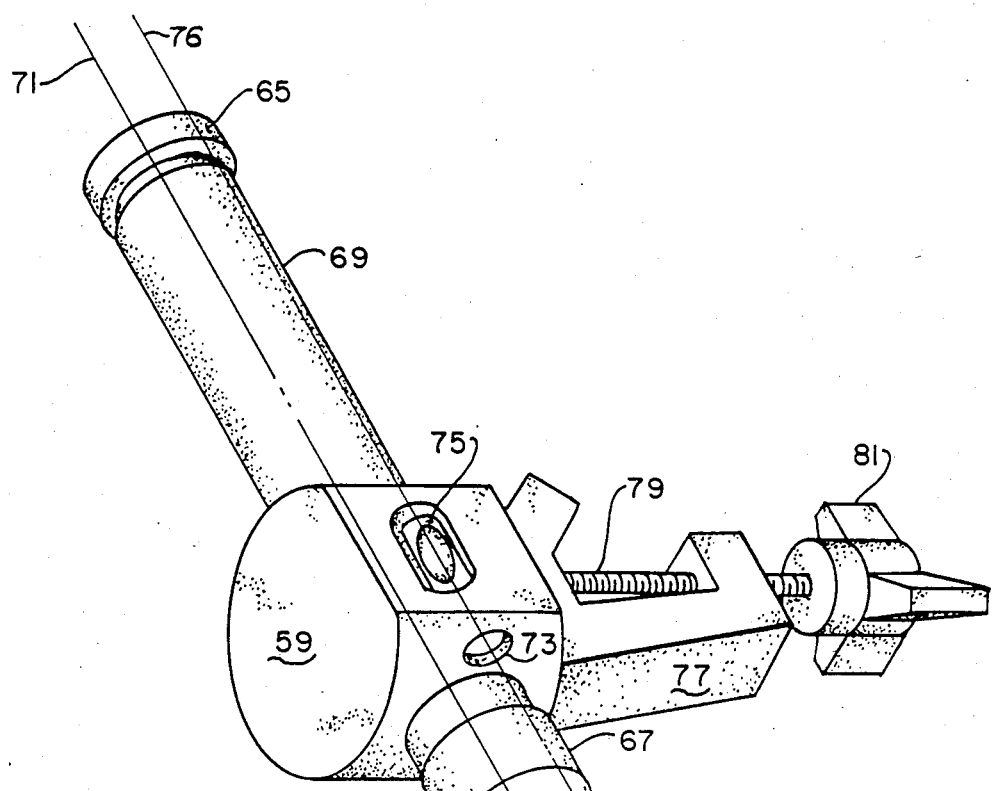
FIG. 5 is a perspective view of the medical apparatus of the present invention.

Medical apparatus 11 (FIG. 5) includes a body portion 59 of suitable material such as a moldable plastic. Body portion 59 includes a pair of coaxial ports. In the first port is secured a light source 61, such as a conventional flashlight having a housing 63. A tube 65 is slidingly secured in the second port. The first port is defined by generally cylindrical protrusion 67 which is internally threaded (see FIG. 8). The second port is defined by an elongate, hollow cylindrical tube 69 of some suitable opaque material such as stainless steel. The inner diameter of tube 69 is sized so as to frictionally engage inner tube 65, but allow sliding movement to focus light from light source 61 into light pattern 37 on the patient. For this reason, body 59 has an interior bore between the first and second ports to allow light to pass from light source 61 down tube 65, and therefrom to the patient. The inner tube 65 and elongate port 69 form a drawtube having an axis 71 which also forms the axis of light source 61 and of light pattern 37.

Body 59 has a second opening 73 therethrough and a third opening 74. A spirit or bubble level 75 is disposed in opening 73 and it is readable through opening 74. The axis 76 of level 75 is parallel to axis 71 of the light pattern source and is held fixed to that axis by body 59. Thus, leveling of level 75 as indicated by the bubble thereof, causes the axis of the light beam to be leveled as well. Rotatably secured to body 59 is means for fixing the medical apparatus vertically on pole 13 or the like. More specifically, this means includes a generally C-shaped member 77 which in use is disposed around the pole. A screw 79, threaded through the base of C-shaped member 77, terminates in a knob 81 to permit the screw to be tightened against pole 13 to hold medical apparatus 11 in place or loosened so as to remove the medical apparatus.

As shown in FIG. 6, medical apparatus 11 is relatively narrow and thus fits easily on pole 13 despite the somewhat crowded conditions on many IV poles in critical care situations. Body 59 is only slightly wider than the light source 61 and the focusing means made up of cylindrical port 69 and tube 65. Body 59 (FIG. 7) also has a cylindrical pivot member 83 protruding outtherefrom. Member 83 is journalled for rotation in C-shaped member 77 so that the body may be rotated as a unit about the axis defined by pivot member 83 to level axis 71 of the light beam source. Pivot member 83 is frictionally engaged in a suitable opening in C-shaped member 77 to hold the body 59 in place once it has been manually rotated to the level position. One end of the C-shaped member adjacent the opening for the pivot member is split, with a screw 85 connecting both parts, so that by suitable adjustment of screw 85 the amount of frictional engagement may be changed as desired.

Figure 8:
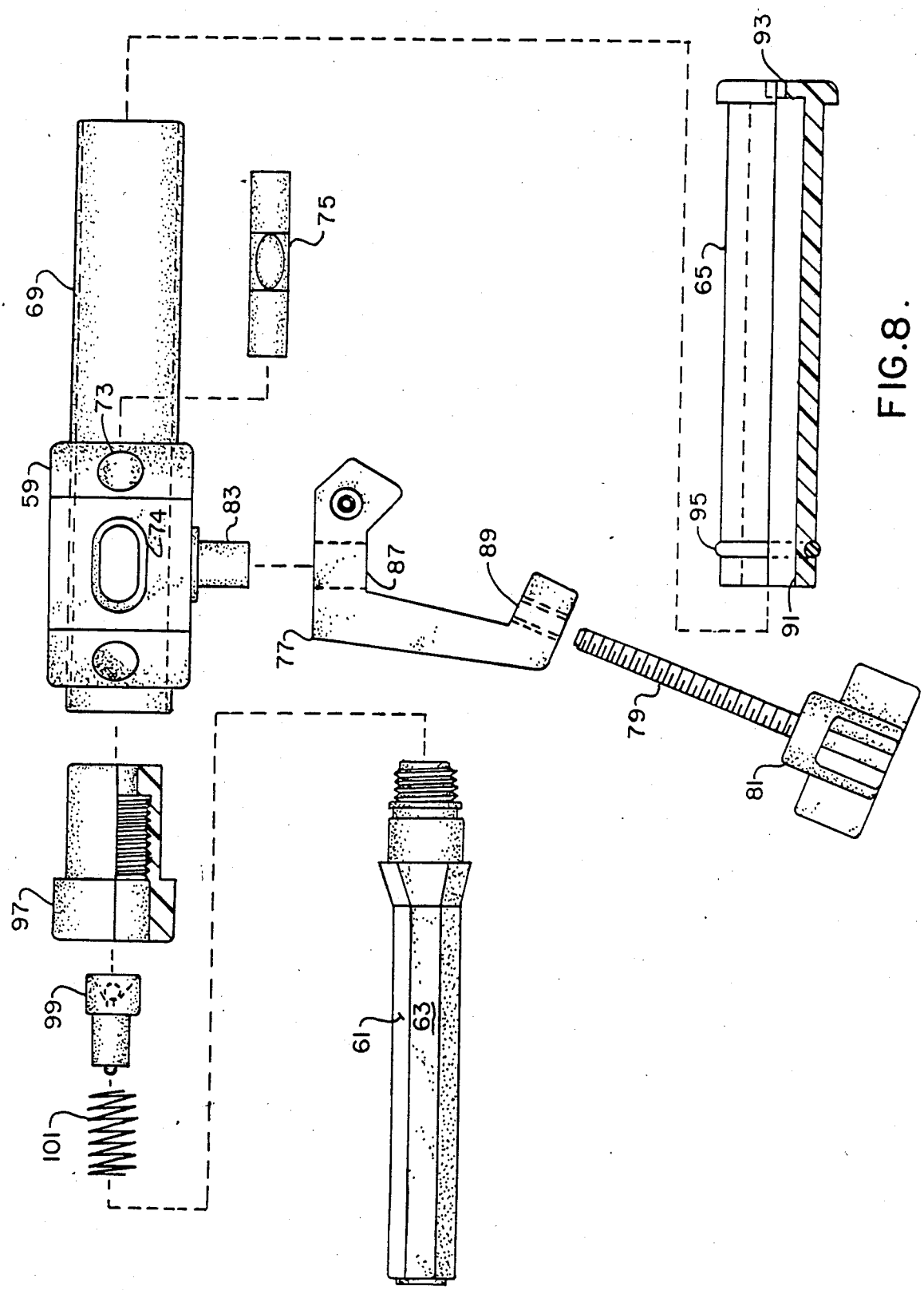
FIG. 8 is an exploded view of the medical apparatus of the present invention.

As seen more clearly in FIG. 8, pivot member 83 includes a shoulder which abuts C-shaped member 77. The main body of pivot member 83 is rotatably journalled in opening 87 of the C-shaped member. Threaded rod 79 is normally disposed in internally threaded opening 89 through C-shaped member 77 at the opposite end thereof from opening 87. Clockwise rotation of rod 79 in the threaded opening results in the rod advancing toward the opposite side of C-shaped member while counterclockwise rotation results in movement of the rod away from opening 87.

Tube 65 has a hollow central portion 91 to permit light to pass from the light source to the proximal end of the tube. A central orifice 93 is disposed in the proximal end of tube 65 to restrict the light passing through the tube and form beam pattern 37. Tube 65 is slidingly movable in its corresponding port so that the beam pattern can be focused on the patient over a wide range of patient-to-transducer distances. If desired, tube 65 could contain some optical elements such as lenses or the like to further focus and form the beam pattern, but this has not been found to be necessary. The relatively simple tube 65 shown results in a beam pattern with the central dark spot on the axis of the beam surrounding by a bright disk. Other patterns could, of course, also be used. An O-ring 95 is disposed in a groove at the distal end of tube 65 to provide an additional seal between tube 65 and hollow cylindrical port 69.

On the lefthand side of body 59, as shown in FIG. 8, the body includes an opening sized to fit an internally-threaded insert 97. Insert 97 is held securely in body 59 and defines port 67. Housing 63 of the light source 61 has mating threads so that the light source is held securely in place with respect to body 59. The housing contains a conventional battery or batteries to provide power for an incandescent lamp 99. A spring 101 is disposed between the batteries and the lamp. When the housing is screwed into insert 97 a predetermined distance, a circuit is completed between the batteries and the lamp and the lamp lights. The lamp is turned off when not in use by unscrewing the housing from the insert a small amount sufficient to break the circuit.

From the above, it will be seen that the method of the present invention includes the steps of fixing light source 61 vertically with respect to the sensor or transducer 21, leveling the light source by rotating body 59 about the axis defined by pivot member 83 until level 75 indicates that level has been reached, shining the light pattern 37 from the source upon the patient, and adjusting the relative position of the patient with respect to the sensor (by moving either the transducer, the patient, or both) until the light pattern strikes a predetermined position on the patient corresponding to the patient's right atrium.

In view of the above, it will be seen that the objects of this invention are achieved and other advantageous results obtained.

As various changes could be made in the above constructions or method without departing from the scope of the invention, it is intended that all matter contained in the above description or shown in the accompanying drawing shall be interpreted as illustrative and not in a limiting sense.

What is claimed is:

1. In a system for measuring internal pressures of a patient, said system including a pressure transducer fixedly mounted with respect to an IV pole or the like, and a catheter having a lumen forming a fluid path between the pressure transducer and a point in the patient at which the pressure is to be measured, the improvement comprising:
   light source means for casting a light pattern upon a patient;
   level means for indicating when the light source means is level;
   a hollow body having at least one port fixedly receiving the light source means and an opening fixedly receiving the level means so that the body holds the light source means and the level means in fixed geometrical relationship with respect to each other;
   a clamp secured to the body for fixedly securing the body to the IV pole or the like at a fixed elevation with respect to the pressure transducer;
   said body being pivotable about an axis defined by the clamp for levelling the light source means once the body is fixedly secured to the IV pole.

2. The system as set forth in claim 1 further including a body having first and second ports adapted to receive the light source means, said light source means including a lamp disposed in the first port of the body and means disposed in the second port for focusing the light from the lamp to form the light pattern.

3. The system as set forth in claim 2 wherein the focusing means includes a drawtube.

4. The system as set forth in claim 3 wherein the longitudinal axis of the drawtube is parallel to the longitudinal axis of the level means.

5. The system as set forth in claim 1 wherein the light source means includes a transversely extending pivot member defining an axis about which the light source means is rotatable, said fixing means having the pivot member rotatably journalled therein, whereby the light source means may be rotated with respect to the fixing means.

6. A medical apparatus comprising:
   light source means for casting a light pattern upon a patient;
   level means for indicating when the light source means is level;
   a hollow body having at least one port fixedly receiving the light source means and an opening fixedly receiving the level means so that the body holds the light source means and the level means in fixed geometrical relationship with respect to each other; and
   a clamp secured to the body for fixedly securing the body to an IV pole or the like at a fixed elevation with respect to a reference;
   said body being pivotable about an axis defined by the clamp for levelling the light source means once the body is fixedly secured to the IV pole.

7. The medical apparatus as set forth in claim 6 further including a body having a first port, said light source means including a housing secured to said first port, said housing containing a lamp and a power source for the lamp, said first port including internal threads matingly engageable with external threads on the end of the housing near the first port, further including means for making electrical connection between the lamp and the power source when the housing thread are engaged a predetermined amount with the port threads.

8. The apparatus as set forth in claim 6 further including a body having first and second ports receiving the light source means, at least one of said ports being generally cylindrical and hollow, a tube slideable longitudinally with respect to the cylindrical port and in frictional engagement therewith, and means disposed at the end of the tube for restricting the light from the light source so as to form the light pattern on the patient.

9. The apparatus as set forth in claim 6 wherein the light source means includes a transversely extending pivot member defining an axis about which the light source means and the level means are rotatable as a unit, said fixing means having the pivot member rotatably journalled therein.

* * * * *